United States Patent
Kamal et al.

(10) Patent No.: US 11,661,391 B2
(45) Date of Patent: May 30, 2023

(54) CONTINUOUS PRODUCTION OF METHYL PENTENONE USING CATION EXCHANGE RESIN IN A FIXED BED REACTOR

(71) Applicants: INDIAN INSTITUTE OF TECHNOLOGY BOMBAY, Mumbai (IN); HARMONY ORGANICS PRIVATE LIMITED, Pune (IN)

(72) Inventors: Sumit Kamal, Mumbai (IN); Rakesh Dhillon, Mumbai (IN); Sanjay Mahajani, Mumbai (IN); Rahul Nabar, Mumbai (IN); Ravi Nangia, Pune (IN)

(73) Assignees: INDIAN INSTITUTE OF TECHNOLOGY BOMBAY, Mumbai (IN); HARMONY ORGANICS PRIVATE LIMITED, Hadapsar (IN)

( * ) Notice: Subject to any disclaimer, the term of this patent is extended or adjusted under 35 U.S.C. 154(b) by 0 days.

(21) Appl. No.: 17/481,753

(22) Filed: Sep. 22, 2021

(65) Prior Publication Data
US 2022/0089517 A1 Mar. 24, 2022

(30) Foreign Application Priority Data
Sep. 22, 2020 (IN) .............................. 202021041062

(51) Int. Cl.
*C07C 45/72* (2006.01)
*B01J 31/00* (2006.01)
*C07C 45/61* (2006.01)
*B01J 8/06* (2006.01)
*B01J 47/02* (2017.01)
*B01J 39/19* (2017.01)

(52) U.S. Cl.
CPC ............... *C07C 45/61* (2013.01); *B01J 8/067* (2013.01); *B01J 39/19* (2017.01); *B01J 47/02* (2013.01); *B01J 2208/00407* (2013.01)

(58) Field of Classification Search
CPC ................................. C07C 45/72; B01J 31/19
See application file for complete search history.

(56) References Cited

U.S. PATENT DOCUMENTS 9,216,935 B2 * 12/2015 Tadepalli ................ C07C 45/45
9,670,123 B2 *  6/2017 Gadhe ..................... C07C 45/82

* cited by examiner

*Primary Examiner* — Sikarl A Witherspoon
(74) *Attorney, Agent, or Firm* — Fox Rothschild LLP

(57) ABSTRACT

Provided herein is a method for producing methyl pentenone (MPO) in high yield in a continuous mode in a fixed bed reactor having a plurality of sidewall injecting ports by reacting excess methyl ethyl ketone (MEK) with acetaldehyde in presence of a cation exchange resin catalyst, wherein the acetaldehyde is injected from the plurality of sidewall injecting ports of the reactor. The method is also effective in reducing the complete consumption of the catalyst during the course of the reaction.

10 Claims, 3 Drawing Sheets

CONTINUOUS PRODUCTION OF METHYL PENTENONE USING CATION EXCHANGE RESIN IN A FIXED BED REACTOR

FIELD OF INVENTION

The present invention relates to a method for production of methyl pentenone (MPO) in a continuous mode. Particularly, the present invention relates to a method for production of methyl pentenone (MPO) by reacting acetaldehyde with methyl ethyl ketone in presence of a heterogenous catalyst in a fixed bed reactor having side-wall injecting ports.

BACKGROUND OF THE INVENTION

Methyl Pent-3-en-2-one (MPO) is an important fine chemical used in Fragrance & Flavor (F&F) industry. Conventionally, MPO is produced industrially by the semi-batch, aldol condensation reaction of methyl ethyl ketone (MEK) and acetaldehyde (AcH) in the presence of 98% sulphuric acid (catalyst). With the current advancement in technology, continuous production unit gives edge over the conventional batch production. With a global, annual demand of MPO exceeding 25,000 tons and tightening environmental regulations, MPO production is a great candidate for development of a continuous, green-process.

Sulfuric acid and other similar acids/bases are commonly used catalysts in the industrial processes of preparation of saturated ketones like MPO. However, this requires expensive corrosion-resistant equipment (glass lined reactors) and requires post-reaction neutralization of spent acid catalyst which produces large quantities of low-value salt containing aqueous solution as effluent. This effluent must then be subjected to energy-intensive evaporation, and subsequently the salt solid waste is disposed in landfills. Hence, waste-treatment costs account for a significant portion of the cost-of-production.

Cation exchange resin (e.g. Amberlyst-15), is a heterogeneous catalyst, and has advantages over sulfuric acid and deals well with problems such as corrosion, salt handing and safety.

CN103804160B discloses use of multiple types of heterogeneous catalysts such as Amberlyst-15, Amberlyst of Rohm and Haas, and LewatitK2620, Purolite SGC650 (H) from Blright Company, and NKC-9 from Nankai University all tested for the production of MPO in semi-batch and immersion immobilized fixed bed reactor. The invention discloses production of MPO in an immersion fixed bed reactor by adding methyl ethyl ketone and Nankai University dry NKC-9 catalyst loaded in the catalyst loading cage, and stored sufficient acetaldehyde in the liquid storage tank (99%). The reaction is heated by steam in a heat exchanger. When the temperature reaches 70° C., acetaldehyde is injected into the bottom of the inner cavity of the catalyst loading cage by a plunger metering pump (5133 g/h), and the time for controlling the input of acetaldehyde is 1 h. After the reaction was continued for 1 h, after the liquid material was completely discharged, the above reaction conditions were continued, and methyl ethyl ketone was added to the reactor, and acetaldehyde was continuously injected at the above rate to carry out the reaction, and the operation was repeated by chromatography. The material obtained after the reaction was determined to have a single pass conversion of butanone of 76%, a selectivity of 3-methyl-3-penten-2-one of 91%, and a part of impurities were formed, and the liquid material was separated by distillation to remove impurities after the reaction. The obtained butanone can be used as a raw material. The product was isolated to give a purity of 97.4% of 3-methyl-3-penten-2-one.

U.S. Pat. No. 9,670,123B2 discloses a process for selectively preparing an unsaturated ketone which is obtained from a reaction of an aldehyde with a ketone followed by dehydration in the same reaction mixture, the process comprising the steps of—mixing an aldehyde with a ketone; passing the mixture of aldehyde and ketone through a fixed bed catalytic reactor comprising polystyrene sulphonated cation resin or polystyrene carbonated cation resin at a temperature of 60-90 degrees C. and at atmospheric pressure for a retention period of 30-50 minutes; to obtain said unsaturated ketone in a yield of at least 70% and a purity of about 99.5%.

U.S. Pat. No. 9,216,935B2 discloses a process for the production of 3-methyl-3-pentene-2-one (3M3P), the process comprising reacting acetaldehyde and methyl ethyl ketone in the presence of a solid acid catalyst in a continuous reactor system, wherein the solid acid catalyst is a solid acid catalyst supported on a polymeric resin, an acid supported on clay, a polymeric perfluorinated resin sulfonic acid, or a combination thereof.

CN108997098A discloses preparation of 3-methyl-3-amylene-2-ketone: 3-halogen butanone contracting glycol obtained in step A and magnesium chips is prepared into Grignard Reagent. Grignard Reagent and acetaldehyde are then subjected to nucleophilic addition, then carried out under conditions of second of acid catalysis and heating Intramolecular dehydration, finished product: 3-methyl-3-amylene-2-ketone. The method disclosed is a complex heterogeneous method for the MPO production.

KR100834963B1 discloses a metal-doped sulfonated cation-exchange resin catalyst and a process for preparing methyl isobutyl ketone using the same, and more particularly, to a catalyst having improved catalytic activity and high selectivity under mild reaction conditions. The process of preparing methyl isobutyl ketone from acetone takes place in reaction schemes 1 to 3. Reaction scheme 1 is a reaction in which an aldehyde condensation reaction of acetone (A)-Hydroxy carbonyl compound (B) is synthesized. The aldol condensation reaction product B in an acid catalyst is reacted with an α, β-unsaturated ketone compound (C), i.e., 4-methyl-3-penten-1-Methyl-4-penten-2-one (iso-MO) is synthesized. The MO and iso-MO are then hydrogenated with a doped metal having a reducing catalytic property in Scheme 3 to produce methyl isobutyl ketone (D), which is a saturated hydrocarbon ketone.

Deactivation of the heterogenous catalysts like cation exchange resin in a reaction is inevitable. There are multiple reasons for catalyst deactivation. It was found that the desulphonation and metal exchange with catalytic ions accounts for nearly 75-80% deactivation and high boiler deposition is responsible for the rest.

Thus, there exists a need for a novel, continuous process for preparation of MPO using a heterogenous catalyst like cation exchange resin as a substitute for mineral acid which not only improves the yield of MPO but also mitigates the deactivation of catalyst and multiple problems of corrosion, safety, salt handing and its disposal.

OBJECT OF THE INVENTION

It is an object of the present invention to overcome the drawbacks of the prior art.

It is another object of the present invention to provide a process for preparation of MPO with an improved yield.

It is a further object of the present invention to provide a method for preparation of MPO using methyl ethyl ketone (MEK), acetaldehyde and cation exchange resin catalyst, which not only improves the yield of pure MPO but also inhibits the deactivation of catalyst.

It is yet another object of the present invention to provide a process for preparation of methyl pentenone by using a heterogeneous catalyst as a substitute for mineral acid.

It is further an object of the present invention to provide a method for minimizing deactivation of a heterogeneous catalyst used in the preparation of methyl pentenone.

SUMMARY OF THE INVENTION

The following disclosure presents a simplified summary of the invention in order to provide a basic understanding of some aspects of the invention. This summary is not an extensive overview of the present invention. It is not intended to identify the key/critical elements of the invention or to delineate the scope of the invention. Its sole purpose is to present some concept of the invention in a simplified form as a prelude to a more detailed description of the invention presented later.

It is an aspect of the present invention there is provides a method for producing methyl pentenone (MPO) in a continuous mode in high yield, the method comprising a reaction between methyl ethyl ketone (MEK) and acetaldehyde in presence of a heterogeneous catalyst in a fixed bed reactor having a plurality of sidewall injecting ports, wherein MEK is fed in a bed of the heterogeneous catalyst in the reactor and acetaldehyde is injected from the plurality of sidewall injecting ports and wherein the concentration of acetaldehyde to methyl ethyl ketone is from 1:3 to 1:18 (feed molar ratio).

In another aspect of the present invention there is provided a continuous method for preparing methyl pentenone in a fixed bed reactor, wherein the method comprises steps of i) feeding methyl ethyl ketone into the reactor containing a bed of heterogenous catalyst; ii) injecting acetaldehyde from a plurality of sidewall injecting ports present in the reactor, wherein the reaction takes place at a temperature of 343-363 K with residence time of 295-345 min, wherein the concentration of acetaldehyde to methyl ethyl ketone is from 1:3 to 1:18, and wherein the heterogeneous catalyst is a cation exchange resin catalyst.

BRIEF DESCRIPTION OF ACCOMPANYING DRAWINGS

The above and other aspects, features and advantages of the embodiments of the present disclosure will be more apparent in the following description taken in conjunction with the accompanying drawings, in which.

DETAILED DESCRIPTION OF THE INVENTION

Figure 1:
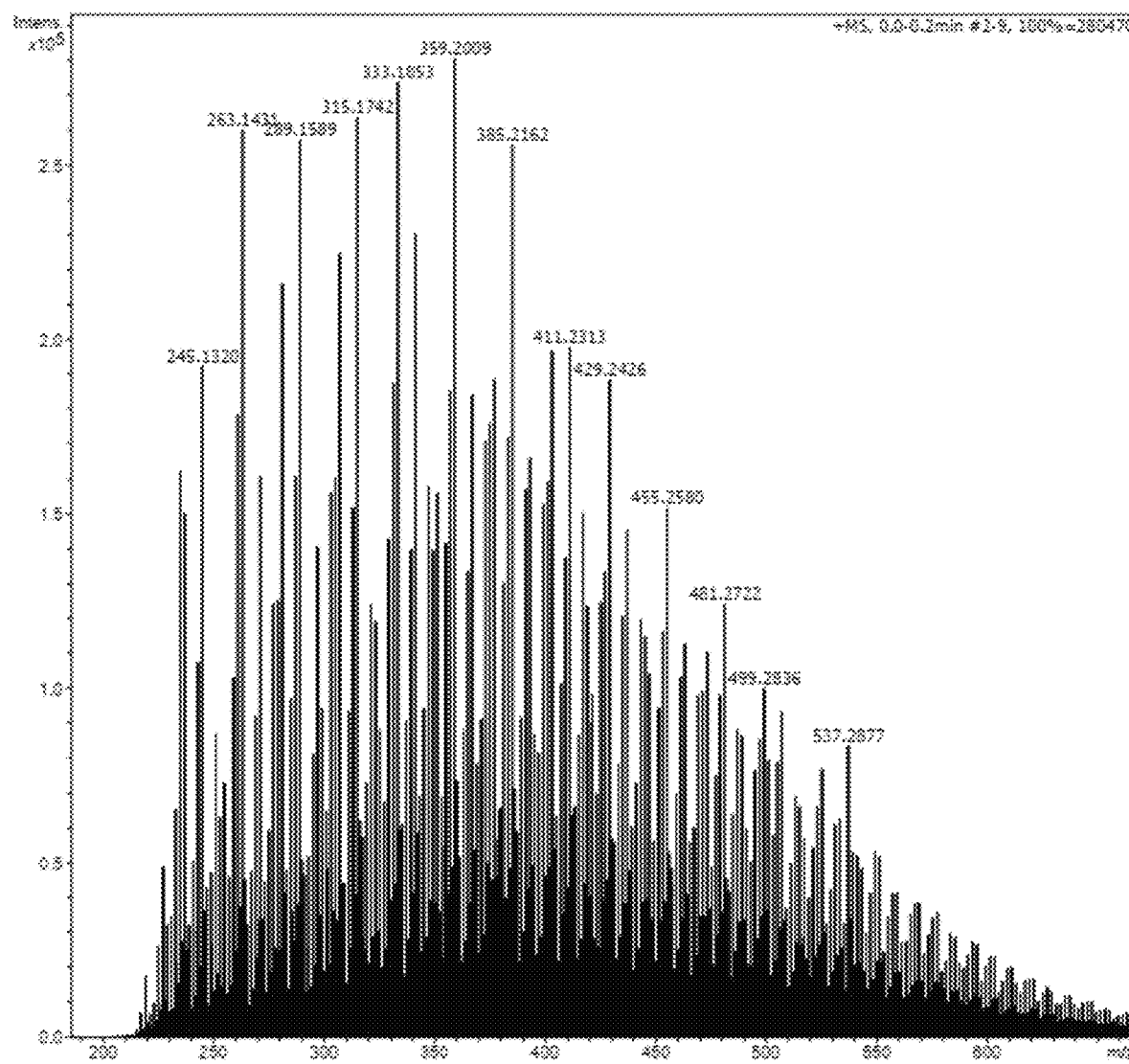
FIG. 1 illustrates HR-LCMS analysis of the oligomers formed in acetaldehyde oligomerization reaction over Amberlyst-15

The present invention is directed to a continuous production method of methyl pentenone (MPO) by using a heterogenous catalyst.

The following description with reference to the accompanying drawings is provided to assist in a comprehensive understanding of various embodiments of the present disclosure as defined by the claims and their equivalents. It includes various specific details to assist in that understanding but these are to be regarded as merely exemplary. Accordingly, those of ordinary skill in the art will recognize that various changes and modifications of the various embodiments described herein can be made without departing from the scope and spirit of the present disclosure. In addition, descriptions of well-known functions and constructions may be omitted for clarity and conciseness.

The terms and words used in the following description and claims are not limited to the bibliographical meanings, but, are merely used by the inventor to enable a clear and consistent understanding of the present disclosure. Accordingly, it should be apparent to those skilled in the art that the following description of various embodiments of the present disclosure is provided for illustration purpose only and not for the purpose of limiting the present disclosure as defined by the appended claims and their equivalents.

It is to be understood that the singular forms "a," "an," and "the" include plural referents unless the context clearly dictates otherwise. Thus, for example, reference to "a component surface" includes reference to one or more of such surfaces.

The terminology used herein is for the purpose of describing particular various embodiments only and is not intended to be limiting of various embodiments. As used herein, the singular forms "a," "an" and "the" are intended to include the plural forms as well, unless the context clearly indicates otherwise. It will be further understood that the terms "comprises" and/or "comprising" used herein specify the presence of stated features, integers, steps, operations, members, components, and/or groups thereof, but do not preclude the presence or addition of one or more other features, integers, steps, operations, members, components, and/or groups thereof. Also, expressions such as "at least one of," when preceding a list of elements, modify the entire list of elements and do not modify the individual elements of the list.

Described herein is a method for preparation of methyl pentenone (MPO) by using a heterogeneous catalyst.

In an embodiment of the present invention, there is provided a method for improving the yield of methyl pentenone (MPO).

The present invention provides a method comprising a reaction between methyl ethyl ketone and acetaldehyde in the presence of a heterogenous catalyst in a fixed bed reactor for producing MPO in high yield.

Yield is defined as follows:

$$\text{Yield} = \frac{\text{Actual moles of } MPO \text{ formed per mole of acetaldehyde consumed}}{\text{Ideal moles of } MPO \text{ formed per mole of acetaldehyde consumed}}$$

In an embodiment there is provided a method for producing methyl pentenone (MPO) in a continuous mode in high yield comprising a reaction between methyl ethyl ketone and acetaldehyde in presence of a heterogeneous catalyst, wherein the reaction takes place in a fixed bed reactor having plurality of sidewall injecting ports.

The method of the present invention results in a high yield of 80% steady state MPO in the pilot scale for nearly 600 hours, wherein the production is based on the concentration of acetaldehyde to methyl ethyl ketone, which is in the range of from 1:3 to 1:18 (AcH:MEK).

The present invention relates to a method for producing methyl pentenone (MPO) in a continuous mode in high yield, the method comprising a reaction between methyl ethyl ketone (MEK) and acetaldehyde in presence of a heterogeneous catalyst in a fixed bed reactor having a plurality of sidewall injecting ports, wherein MEK is fed in a bed of the heterogeneous catalyst in the reactor and acetaldehyde is injected from the plurality of sidewall injecting ports and wherein the concentration of acetaldehyde to methyl ethyl ketone is from 1:3 to 1:18 (feed molar ratio).

In an embodiment of the present invention, the reaction conditions or parameters like temperature, flow rate, and residence time play an important role in controlling the yield of MPO.

In an embodiment of the present invention there is provided various reaction conditions which governs the yield of MPO in a reaction between acetaldehyde and methyl ethyl ketone in a fixed bed reactor.

The present invention provides that, relative improvement in MPO selectivity is insignificant beyond 363 K. Accordingly, in an implementation the present method is carried out in the temperature range of 343-363 K. This range is critical because the MPO yield increases with temperature.

The present invention thus provides a method for production MPO in high yield, wherein the reaction is performed at a temperature of 343-363 K.

In a further embodiment of the present invention, feed molar ratio shows prominent effect over MPO selectivity.

It was found by the inventors that the steady state MPO yield for 1:3 feed ratio is only 67% (based on acetaldehyde) which increases up to 81% (based on acetaldehyde) for 1:10 and 84% (based on acetaldehyde) for 1:18 feed ratio in a fixed bed reactor with no sidewall injection.

In an embodiment, where the reactions were performed using side injection of acetaldehyde from multiple side ports of the reactor the local feed concentration varies in the range of 1:11 to 1:18 when overall feed concentration was fixed at 1:3 (AcH:MEK). It was surprisingly found that in a fixed bed reactor where the acetaldehyde is injected through the sidewalls, the yield is 79% at 1:3 feed ratio and increased to 83% at 1:3.5 feed ratio.

The method thus employing side wall injection of acetaldehyde attains the same yield of MPO at 1:3 feed ratio as compared to 1:10 feed ratio where there is no side wall injection of acetaldehyde.

Therefore, the present invention provides a method for preparing MPO in high yield, wherein the feed molar ratio of acetaldehyde to MEK varies from 1:3 to 1:18 (AcH: MEK).

The inventors of the present invention have observed that the MPO yield increases from 55% to 85% by minimizing the acetaldehyde concentration with respect to MEK or in other words by increasing the concentration of MEK with respect to acetaldehyde.

In another embodiment there is provided that residence time play an important role in the overall process development.

As used herein "Residence time" is defined as volume of catalyst fed in the fixed bed reactor divided by the feed volumetric flow rate.

It was further found by the present inventors that due to the low boiling point of acetaldehyde (291 K), it is difficult to recover the unconsumed acetaldehyde. Therefore, the overall residence time for fixed bed reactor is fixed at 295-345 min to ensure the complete conversion of acetaldehyde which has significant effect over MPO yield.

Therefore, the present invention provides a method for preparation of MPO, wherein the overall residence time for fixed bed reactor is fixed at 295-345 min.

In another embodiment of the present invention there is provided a method for preparation of MPO in high yield by controlling the concentration of acetaldehyde and MEK in the reactor.

In an embodiment of the present invention there is provided a method for preparation of MPO by using a heterogeneous catalyst.

The present invention aims to mitigate the problem of corrosion caused by a mineral acid such as sulfuric acid when used as a catalyst in the preparation of MPO.

The existing process for the production of MPO is associated with the use of homogeneous catalysts, giving limited yields and imparting excessive load on the effluent treatment thereby making the process environment unfriendly.

The present invention provides a process for preparation of MPO comprising heterogeneous catalysts selected from the group of: Polystyrene sulphonated cation resin, Polymeric resin, Solid catalyst supported on clay, Solid acid catalyst supported on polymeric resin, solid aluminophosphate, Amberlyst-15, Amberlyst-35, Langson dry Lewatit K2620 catalyst, Dry NKC, Dry purolite, Zinc acetate, zinc acetate dehydrate, aluminium phosphate.

In a most preferred embodiment, there is provided a method for production of MPO in high yield, wherein the reaction takes place in between an excess of MEK and acetaldehyde in presence of cation exchange resin, Amberlyst-15.

The heterogeneous catalysts are often associated with problems such as catalyst deactivation during the course of the reaction.

The inventors of the present invention have observed that heterogeneous catalysts improve the yield of MPO for a limited time and after a certain time period the catalysts starts deactivating and further suppressing the yield of MPO.

In an embodiment of the present invention there is provided a method for preparation of MPO in presence of heterogeneous catalyst with a controlled deactivation of heterogeneous catalysts.

The inventors of the present invention propose that most of the metals (in ppm) travelling along with the feed are trapped in the guard column, which significantly control the deactivation of subsequent columns.

The present invention provides a solution to minimize the blockage of column in the method for preparation of MPO, wherein the method comprises injection of acetaldehyde from the sidewall of the reactor.

In an embodiment of the present invention when acetaldehyde is injected from the multiple sidewalls of the reactor containing excess of MEK, less amount of oligomers are generated and additionally, the overall oligomers concentration is low due to abundance of MEK. Due to this reason, blockage of the catalyst active sites will be less and hence catalysts deactivation is also less.

As used herein "Oligomers" are formed by the repeated aldol condensation reaction of acetaldehyde with itself by repeating the acetaldehyde molecule for 'n' times, where n varies from 6 to 13. Molecular weight distribution of the oligomers formed during the reaction varies in the range of 300-500 a.m.u. HR-LCMS result showing molecular weight distribution of the oligomers usually formed are shown in FIG. 1. All possible oligomers produced are shown in Table 1.

TABLE 1

| S.No. | Chemical name | Structure | Observed m/z |
|---|---|---|---|
| 1 | 5,7,9,11-tetrahydroxydodec-2-enal | 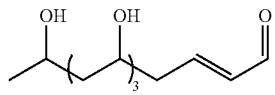 | 246 |
| 2 | 3,5,7,9,11-pentahydroxydodecanal | 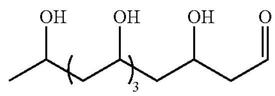 | 264 |
| 3 | 5,7,9,11,12-pentahydroxytetradec-2-enal | 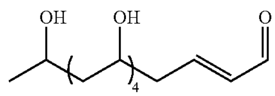 | 290 |
| 4 | 7,9,11,12,13-pentahydroxyhexadec-2,4-dienal | 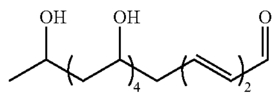 | 316 |
| 5 | 5,7,9,11,13,15-hexahydroxyhexadec-2-enal | 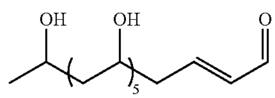 | 334 |
| 6 | 7,9,11,13,15,17-hexahydroxyoctadeca-2,4-dienal | 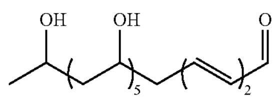 | 360 |
| 7 | 9,11,13,15,17,19-hexahydroxyicosa-2,4,6-trienal | 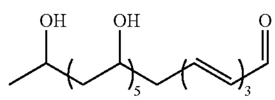 | 386 |
| 8 | 11,13,15,17,19,21-hexahydroxydocasa-2,4,6,8-tetraenal | 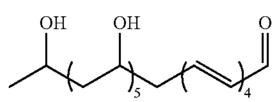 | 412 |
| 9 | 9,11,13,15,17,19,21-heptahydroxydocasa-2,4,6-trienal | 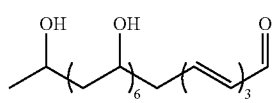 | 430 |
| 10 | 11,13,15,17,19,21,23-heptahydroxytetracosa-2,4,6,8-tetraenal | 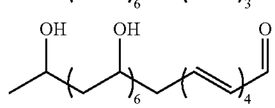 | 456 |
| 11 | 13,15,17,19,21,23,25-heptahydroxyhexacosa-2,4,6,8,10-pentaenal | 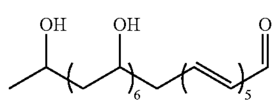 | 482 |
| 12 | 11,13,15,17,19,21,23,25-octahydroxyhexacosa-2,4,6,8-tetraenal | 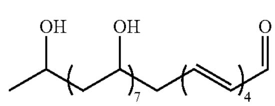 | 500 |
| 13 | 7,9,11,13,15,17,19,21,23,25-decahydroxyhexacosa-2,4-dienal | 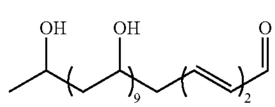 | 536 |

The present invention thus provides a method for production of MPO which prevents formation of excess oligomers by providing abundance of methyl ethyl ketone and small amount of acetaldehyde in the reactor and thereby preventing the complete deactivation of catalyst.

Therefore, in an embodiment of the present invention there is provided a method for minimizing the deactivation of a heterogeneous catalyst in a reaction between acetaldehyde and MEK for preparing MPO, wherein the concentration of acetaldehyde to methyl ethyl ketone is from 1:3 to 1:18, and wherein the acetaldehyde is introduced from the side walls of the fixed bed reactor.

Therefore, in an embodiment of the present invention, there is provided a continuous method for preparation of MPO with an increased yield and minimum wastes.

In an embodiment of the present invention there is provided a method for preparation of MPO in a continuous mode in a fixed bed reactor having plurality of sidewall injecting ports.

It was found by the inventors that a plurality of sidewall injection of acetaldehyde and an excess of MEK in the reactor results in improving the yield of MPO by reducing the deactivation of catalyst.

The method as described herein results in a yield of methyl pentenone in the range of 65% to 85% with respect to the amount of acetaldehyde.

In a preferred embodiment, there is provided a continuous method for preparing methyl pentenone in a fixed bed reactor, wherein the method comprises steps of i) feeding methyl ethyl ketone into the reactor containing a bed of heterogenous catalyst;

ii) injecting acetaldehyde from a plurality of sidewall injecting ports present in the reactor, wherein the reaction takes place at a temperature of 343-363 K with residence time of 295-345 min, wherein the concentration of acetaldehyde to methyl ethyl ketone is from 1:3 to 1:18, and wherein the heterogeneous catalyst is a cation exchange resin catalyst.

Figure 2:
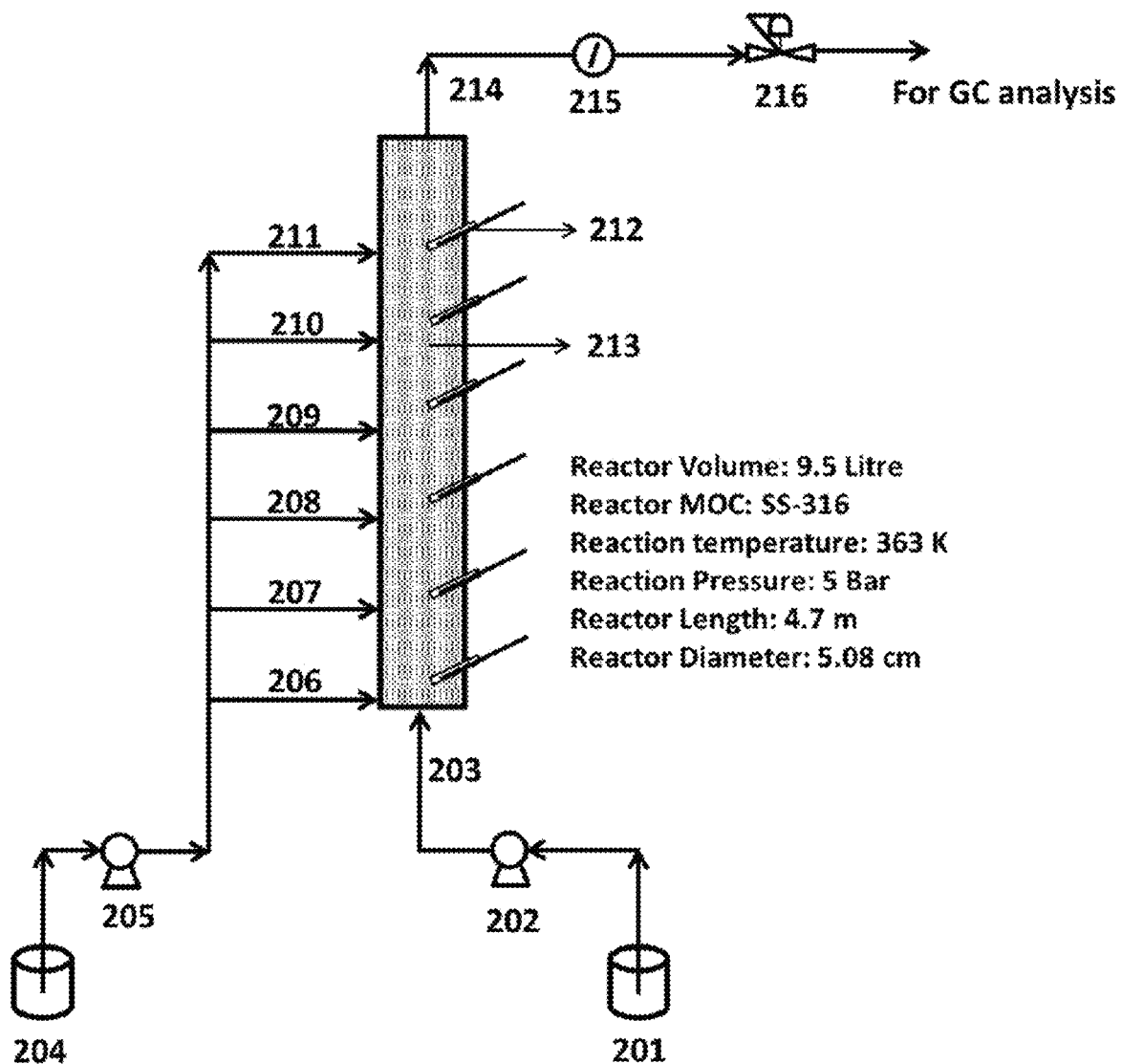
FIG. 2 illustrates process flow diagram in the case of side injection of acetaldehyde in the fixed bed reactor (FBR) in accordance with the present invention

In an embodiment, the present invention provides a continuous method for preparation of MPO, wherein the reaction takes place in a fixed bed reactor and wherein the reactor has plurality of side wall injecting ports as shown in FIG. 2. In a non-limiting embodiment, the fixed bed reactor with side wall injecting ports has at least the following units:

| S. No. | Reference number | Unit |
| --- | --- | --- |
| 1 | 201 | MEK feed tank |
| 2 | 202 | MEK feed diaphragm pump, P1 |
| 3 | 203 | Main inlet line |
| 4 | 204 | AcH feed tank |
| 5 | 205 | AcH feed diaphragm pump, P2 |
| 6 | 206 | Side injection port, S1 |
| 7 | 207 | Side injection port, S2 |
| 8 | 208 | Side injection port, S3 |
| 9 | 209 | Side injection port, S4 |
| 10 | 210 | Side injection port, S5 |
| 11 | 211 | Side injection port, S6 |
| 12 | 212 | Temperature sensor |
| 13 | 213 | Amberlyst-15 bed |
| 14 | 214 | Outlet line |
| 15 | 215 | Pressure gauge |
| 16 | 216 | Back Pressure Regulator |

Figure 3:
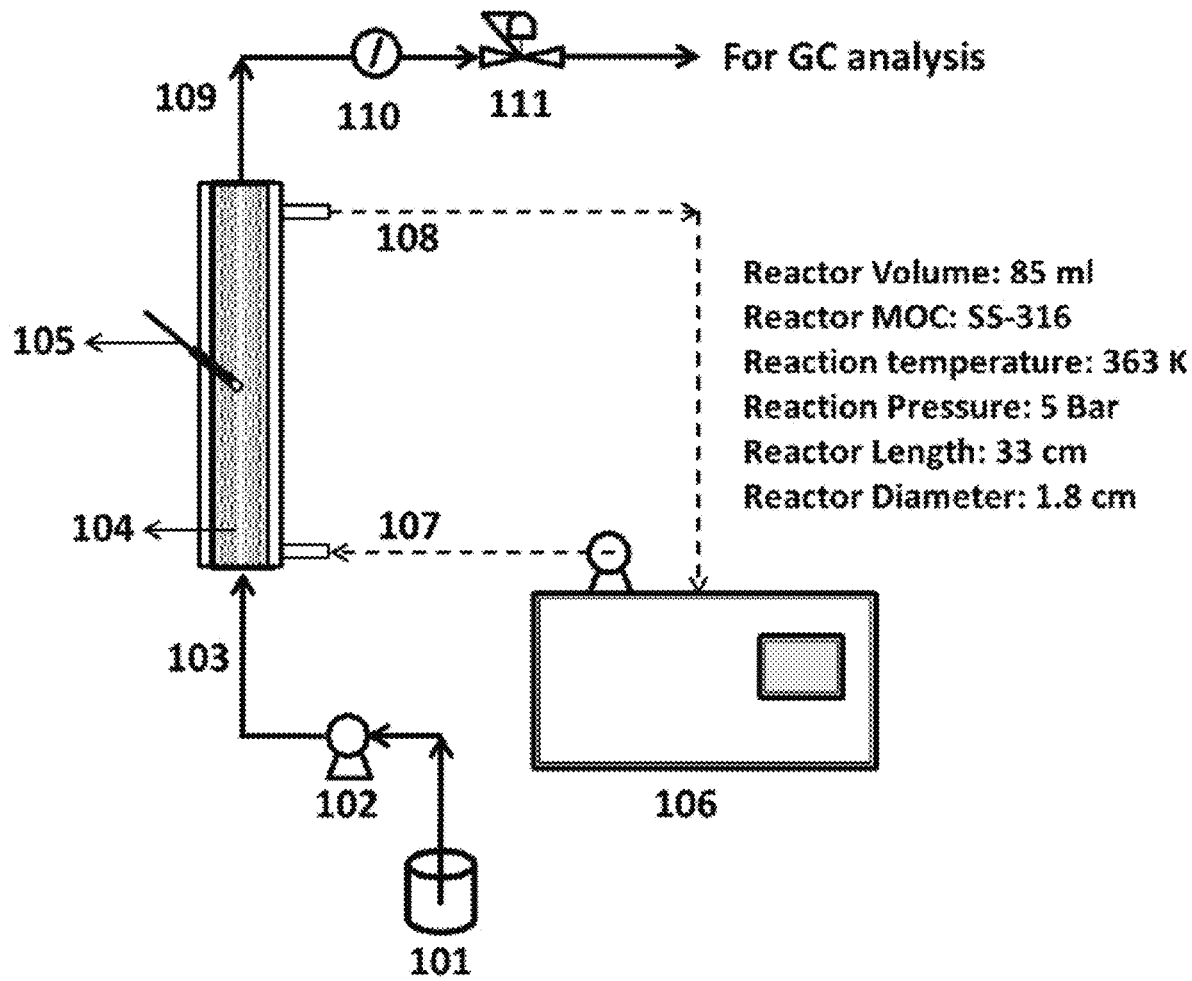
FIG. 3 illustrates process flow diagram for the method without side injection walls in the reactor

In a comparative embodiment, there is also provided a method for preparation of MPO comprising a reaction between methyl ethyl ketone and acetaldehyde in presence of a catalyst, wherein the reaction is performed at a temperature of 343-363 K with residence time of 8-50 min and wherein the concentration of acetaldehyde to the methyl ethyl ketone ranges from 1:3 to 1:18 (AcH:MEK). This method takes place in a fixed bed reactor as illustrated in FIG. 1 without side injection ports. The fixed bed reactor without side wall injecting ports as shown in FIG. 3 has at least the following units:

| S. No. | Reference number | Unit |
| --- | --- | --- |
| 1 | 101 | Feed tank |
| 2 | 102 | Feed diaphragm pump |
| 3 | 103 | Feed inlet line |
| 4 | 104 | Amberlyst-15 bed |
| 5 | 105 | Temperature sensor |
| 6 | 106 | High temperature oil bath |
| 7 | 107 | Hot oil inlet line |
| 8 | 108 | Hot oil outlet line |
| 9 | 109 | Reaction Mixture outlet Line |
| 10 | 110 | Pressure gauge |
| 11 | 111 | Back Pressure Regulator (BPR) |

In an exemplary embodiment of the present invention, the present method as described herein is carried out in a fixed bed reactor with side wall injection ports as illustrated in FIG. 2 and described above. However, any modifications to the fixed bed reactor is also within the scope of a person skilled in the art.

In an embodiment, the method of the present invention is performed on the pilot scale FBR with 5-6 side injecting ports. Weight hourly space velocity (WHSV) is the basis for scale up in the absence of heat and mass transfer resistance. Pilot level experiments are performed at the scale up volume ratio of 1:120.

Advantage of the Invention

The current invention has a potential to eliminate several expensive operations of conventional MPO processing. In addition, the method is effective in saving on the expensive, corrosion resistant glass lined equipment and additional investments needed for neutralization and Multi Effect Evaporation. The current process also has a potential to improve yields which will add to its economic potential.

Henceforth, embodiments of the present disclosure are explained with one or more examples. However, such examples are provided for the illustration purpose for better understanding of the present disclosure and should not be construed as limitation on scope of the present disclosure.

EXAMPLES

Main Example 1

A fixed bed reactor of stainless steel, SS-316 (length 470 cm, inner diameter 5.08 cm) is used for the reaction. Reactor is filled with the catalyst Amberlyst-15 (3.15 kg). MEK is fed to the reactor at 8.67 gm/min in the main line using pump. Acetaldehyde is sent to the column through 6 side injection ports at 0.9 gm/min (MEK 55.56% (w/w)) as shown in the FIG. 2. Experiment was performed at overall feed ratio of 1:3 (AcH:MEK) at an overall feed flow rate of 18-18.5 kg per day (295 min of residence time) at 363-368 K and 5 bar (gauge). Reactor was heated using electric coil wrapped over the reactor column. Experiments was performed for 300 hours continuously. It was found that for the 300 hours when average feed molar ratio is nearly 1:3 (AcH:MEK), MPO yield varied in the range of 75-80% (based on acetaldehyde). MPO yield was verified by the distillation. This result was very important because it demonstrates the extended use of Amberlyst-15 for production of methyl pentenone at industrial scale because of catalyst thermal, chemical and mechanical stability.

(Amount of reactant/catalyst: Catalyst=3.15 kg, Total Feed=228.75 kg (AcH=38.71 kg and MEK=190.04 kg), MPO produced=68.97 kg)

Main Example 2

A fixed bed reactor of stainless steel, SS-316 (length 470 cm, inner diameter 5.08 cm) is used for the reaction. Reactor is filled with the catalyst Amberlyst-15 (3.15 kg). MEK is fed to the reactor at 8.67 gm/min in the main line using pump. Acetaldehyde is sent to the column through 6 side injection ports at 0.71 gm/min (MEK 55.56% (w/w)) as shown in the FIG. 2. Experiment was performed at overall feed ratio of 1:3.5 (AcH:MEK) at an overall feed flow rate of 18-18.5 kg per day (345 min of residence time) at 363-368 K and 5 bar (gauge). Reactor was heated using electric coil wrapped over the reactor column. Experiments was performed for 300 hours on a continuously. It was found that MPO yield varied in the range of 80-85% (based on acetaldehyde). MPO yield was verified by the actual distillation. This result was very important because it demonstrate the extended use of Amberlyst-15 for production of methyl pentenone at industrial scale because of catalyst thermal, chemical and mechanical stability.

(Amount of reactant/catalyst: Catalyst=3.15 kg, Total Feed=228.75 kg (AcH=34 kg and MEK=194.75 kg), MPO produced=62.85 kg)

Comparative Example 1

An experiment is performed at 1:3 (AcH:MEK) feed molar ratio at 363 K, 5 bar (gauge) and 1 ml/min of flow rate (50 min of residence time) for 180 hours in a simple fixed bed reactor (height: 35 cm and internal diameter 1.5 cm, FIG. 1) having no sidewall injecting ports. It was found from the experiment that MPO yield is constant only up to first 30 hours, after that it has decreased from 65% to nearly 40% (based on acetaldehyde) at the end of 180 hours. This justifies the decrement in MPO selectivity because of catalyst deactivation.

(Amount of reactant/catalyst: Catalyst=30 g, Total Feed=8640 g (AcH=1462.15 g and MEK=7177.85 g), MPO produced=1750 g)

Comparative Example 2

Another experiment was performed at 1:10 (AcH:MEK) feed molar ratio at 363 K, 5 bar (gauge) and 1 ml/min of flow rate (50 min of residence time) for 180 hours in a fixed bed reactor (height: 35 cm and internal diameter 1.5 cm, FIG. 1) having no sidewall injecting ports. It was found from the experiment that, MPO yield was constant at 81% (based on acetaldehyde) till the end of $180^{th}$ hours. This justifies that MPO yield is stable with time at lower concentration of acetaldehyde compared with MEK.

(Amount of reactant/catalyst: Catalyst=30 g, Total Feed=8640 g (AcH=497.6 g and MEK=8142.4 g), MPO produced=900 g)

Comparative Example 3

Another experiment was performed at 1:18 (AcH:MEK) feed molar ratio at 363 K, 5 bar (gauge) and 1 ml/min of flow rate (50 min of residence time) for 12 hours in a fixed bed reactor (height: 35 cm and internal diameter 1.5 cm, FIG. 1). It was found from the experiment that, MPO yield was constant at 84% (based on acetaldehyde) till the end of $12^{th}$ hours.

(Amount of reactant/catalyst: Catalyst=30 g, Total Feed=576 g (AcH=18.91 g and MEK=557.09 g), MPO produced=35.37 g)

Comparative Example 4

Comparative Example Reaction with Amberlyst-15 vs. Sulfuric Acid for the Self-Aldol Reaction of MEK Example 4A: An experiment was performed in an SS-316 batch reactor using 100 g pure methyl ethyl ketone (MEK) at 343 K and 10 g Amberlyst-15 for 6 hours. MEK loss due to self-aldol reactions was barely 4-5% by the formation of 4-5 gm 5-methyl-4-hepten-3-one as evident from GC-FID. The volume of the batch reactor used in the reaction was 250 ml in which 125 ml MEK was taken.

Example 4B: An experiment was performed in a glass reactor using 100 g pure methyl ethyl ketone (MEK) at 343 K and 10 g sulfuric acid for 6 hours. MEK loss due to self-aldol reactions was nearly 14-15% by the formation of 7-8 gm 5-methyl-4-hepten-3-one as evident from GC-FID and other 7-8 gm by the oligomers which was obtained by mass balance. The volume of the glass reactor was 250 ml in which 125 ml MEK was taken.

MEK loss in the side products in Amberlyst-15 is very low (4-5%), which is likely to give an edge to cation exchange resin over homogeneous sulfuric acid catalyst. In the presence of sulfuric acid, 14-15% (w/w) MEK undergoes a self-aldol reaction.

Comparative Example 5

Comparative Example Reaction with Amberlyst-15 vs. Sulfuric Acid for the Self-Aldol Reaction of MPO Example 5A: An experiment was performed in an SS-316 batch reactor using 100 g pure methyl pentenone (MPO) at 343 K and 10 g Amberlyst-15 for 6 hours. MPO loss due to self-aldol reactions was negligible due to no reaction. Volume of the batch reactor was 250 ml in which 115 ml MPO was taken.

Example 5B: An experiment was performed in a glass reactor using 100 g pure methyl pentenone (MPO) at 343 K and 10 g sulfuric acid for 6 hours. MPO loss due to self-aldol reactions was nearly 14-15% by the formation of 14-15 gm oligomers which was obtained by mass balance. Volume of the glass reactor was 250 ml in which 125 ml MPO was taken.

MPO loss in the side products in Amberlyst-15 is negligible, which is likely to give an edge to cation exchange resin over homogeneous sulfuric acid catalyst. In the presence of sulfuric acid, 14-15% (w/w) MPO undergoes a self-aldol reaction.

The present invention is not to be limited in scope by the specific embodiments described herein. Indeed, various modifications of the invention, in addition to those described herein, will become apparent to those skilled in the art from the foregoing description and accompanying figures. Such modifications are intended to fall within the scope of the appended claims. The invention is, therefore, to be limited only by the terms of the appended claims along with the full scope of equivalents to which the claims are entitled.

We claim:

1. A method for producing methyl pentenone (MPO) in a continuous mode in high yield, the method comprising a reaction between methyl ethyl ketone (MEK) and acetaldehyde in presence of a heterogeneous catalyst in a fixed bed reactor having a plurality of sidewall injecting ports, wherein MEK is fed in a bed of the heterogeneous catalyst in the reactor and acetaldehyde is injected from the plurality of sidewall injecting ports and wherein the concentration of acetaldehyde to methyl ethyl ketone is from 1:3 to 1:18 (feed molar ratio).

2. The method as claimed in claim 1, wherein the heterogeneous catalyst is a cation exchange resin catalyst.

3. The method as claimed in claim 2, wherein the cation exchange resin catalyst is selected from the group consisting of polystyrene sulphonated cation resin, a polymeric resin, a solid catalyst supported on clay, a solid acid catalyst supported on polymeric resin, solid aluminophosphate, zinc acetate, zinc acetate dehydrate, and aluminium phosphate.

4. The method as claimed in claim 1, wherein the reaction takes place at a temperature of 343-363 K.

5. The method as claimed in claim 1, wherein the reaction takes place at a residence time of 295-345 min.

6. The method as claimed in claim 1, wherein injection of acetaldehyde from the plurality of sidewall injecting ports reduces the production of oligomers in the reactor.

7. The method as claimed in claim 6, wherein the reduced oligomer concentration inhibits the deactivation of catalyst.

8. A continuous method for preparing methyl pentenone in a fixed bed reactor, wherein the method comprises steps of i) feeding methyl ethyl ketone into the reactor containing a bed of heterogenous catalyst;

ii) injecting acetaldehyde from a plurality of sidewall injecting ports present in the reactor, wherein the reaction takes place at a temperature of 343-363 K with residence time of 295-345 min, wherein the concentration of acetaldehyde to methyl ethyl ketone is from 1:3 to 1:18, and wherein the heterogeneous catalyst is a cation exchange resin catalyst.

9. The method as claimed in claim 1, wherein the yield of methyl pentenone is in the range of 65% to 85% with respect to the amount of acetaldehyde.

10. The method as claimed in claim 8, wherein the yield of methyl pentenone is in the range of 65% to 85% with respect to the amount of acetaldehyde.

* * * * *